United States Patent [19]

Bierman

[11] Patent Number: 5,637,098

[45] Date of Patent: Jun. 10, 1997

[54] CATHETER SECUREMENT DEVICE

[75] Inventor: Steven F. Bierman, Del Mar, Calif.

[73] Assignee: Venetec International, Inc., Mission Viejo, Calif.

[21] Appl. No.: 512,082

[22] Filed: Aug. 7, 1995

[51] Int. Cl.$^6$ ................................................ A61M 5/32
[52] U.S. Cl. .................... 604/180; 604/174; 128/DIG. 26
[58] Field of Search ...................................... 604/174, 179, 604/180, 177; 128/DIG. 26, 912; 606/232, 228, 229, 230, 233

[56] References Cited

U.S. PATENT DOCUMENTS

| | | |
|---|---|---|
| 2,707,953 | 5/1955 | Ryan . |
| 3,046,984 | 7/1962 | Eby . |
| 3,059,645 | 10/1962 | Hasbrouck et al. . |
| 3,556,096 | 1/1971 | Fuller . |
| 3,677,250 | 7/1972 | Thomas . |
| 3,973,565 | 8/1976 | Steer . |
| 4,020,835 | 5/1977 | Nordstrom et al. . |
| 4,057,066 | 11/1977 | Taylor ............................ 604/180 |
| 4,059,105 | 11/1977 | Cutruzzula et al. . |
| 4,133,307 | 1/1979 | Ness . |
| 4,142,527 | 3/1979 | Garcia . |
| 4,449,975 | 5/1984 | Perry ............................ 604/179 |
| 4,453,933 | 6/1984 | Speaker ............................ 604/179 |
| 4,633,863 | 1/1987 | Filips et al. ............................ 604/240 |
| 4,650,473 | 3/1987 | Bartholomew et al. .......... 128/DIG. 26 |
| 4,711,636 | 12/1987 | Bierman ............................ 604/180 |
| 4,919,654 | 4/1990 | Kalt ............................ 604/180 |
| 4,950,285 | 8/1990 | Wilk ............................ 606/232 |
| 5,000,741 | 3/1991 | Kalt ............................ 604/180 |
| 5,037,397 | 8/1991 | Kalt et al. ............................ 604/174 |
| 5,073,170 | 12/1991 | Schneider ............................ 604/180 |
| 5,098,399 | 3/1992 | Tollini ............................ 604/180 |
| 5,123,913 | 6/1992 | Wilk et al. ............................ 606/232 |
| 5,147,322 | 9/1992 | Bowen et al. ............................ 604/180 |
| 5,192,273 | 3/1993 | Bierman et al. ............................ 604/174 |
| 5,192,274 | 3/1993 | Bierman ............................ 604/180 |
| 5,195,981 | 3/1993 | Johnson ............................ 604/180 |
| 5,224,935 | 7/1993 | Hollands .......... 128/DIG. 26 |
| 5,266,401 | 11/1993 | Tollini ............................ 428/343 |
| 5,267,967 | 12/1993 | Schneider ............................ 604/174 |
| 5,282,463 | 2/1994 | Hammersley .......... 128/DIG. 26 |
| 5,292,312 | 3/1994 | Delk et al. ............................ 604/180 |
| 5,304,146 | 4/1994 | Johnson et al. ............................ 604/180 |
| 5,342,317 | 8/1994 | Claywell ............................ 604/179 |
| 5,354,282 | 10/1994 | Bierman ............................ 604/180 |
| 5,395,344 | 3/1995 | Beisang, III et al. ................ 604/180 |
| 5,413,562 | 5/1995 | Swauger ............................ 604/179 |
| 5,443,460 | 8/1995 | Miklusek ............................ 604/282 |
| 5,456,671 | 10/1995 | Bierman ............................ 604/180 |

(List continued on next page.)

FOREIGN PATENT DOCUMENTS

| | | |
|---|---|---|
| 0 274 418 A2 | 7/1988 | European Pat. Off. . |
| 0 470 709 A1 | 2/1992 | European Pat. Off. . |
| 31 10 023 A1 | 9/1982 | Germany . |
| 88 11 131.8 | 2/1989 | Germany . |
| 2 219 034 | 11/1989 | United Kingdom . |
| WO80/01458 | 1/1980 | WIPO . |
| WO92/19309 | 5/1992 | WIPO . |

Primary Examiner—Michael Buiz
Assistant Examiner—Patrick W. Rasche
Attorney, Agent, or Firm—Knobbe, Martens, Olson & Bear LLP

[57] ABSTRACT

An anchoring system includes a simply structured suture-like device which permits a fluid tube or similar article to be easily attached to the patient without the use of needles and without actually suturing anything to the patient. The anchoring device desirably includes two threads or filaments and two corresponding receptacles. The filaments include protuberances which cooperate with apertures of the receptacles to permit easy insertion of the distal end of the filaments into the receptacles, but inhibit retraction of the filament distal ends from the receptacles. A healthcare provider simply wraps the filament around the fluid tube and then threads the distal end of the filament through the receptacle aperture until the filament holds the tube tightly against a base of the anchoring system. The base in turn includes an adhesive bottom surface which can be attached to the patient's skin.

24 Claims, 3 Drawing Sheets

U.S. PATENT DOCUMENTS

| | | | |
|---|---|---|---|
| 5,468,228 | 11/1995 | Gebert | 604/174 |
| 5,468,230 | 11/1995 | Corn | 604/110 |
| 5,468,231 | 11/1995 | Newman et al. | 604/180 |
| 5,496,282 | 3/1996 | Militzer et al. | |
| 5,520,656 | 5/1996 | Byrd. | |
| 5,522,803 | 6/1996 | Teissen-Simony. | |
| 5,527,293 | 6/1996 | Zamierowski. | |
| B1 5,147,322 | 1/1996 | Bowen et al. | 604/180 |

CATHETER SECUREMENT DEVICE

BACKGROUND OF THE INVENTION

1. Field of the Invention

The present invention relates to an anchoring system for anchoring medical article, such as, for example, catheters, fluid supply and drainage tubes, pacemaker and transducer wires and the like to the body of a patient.

2. Description of Related Art

It is very common in the treatment of patients to utilize intravenous (IV) catheters to introduce fluids and medications directly into the bloodstream. In many cases, and particularly with respect to cardiac therapy, the IV catheter is introduced into a central or larger vein located close to the patient's heart. For example, a typical catheter utilized in connection with a central vein is referred to as a "central venous catheter" ("CVC"), while a venous catheter peripherally inserted into the central circulation through a vein in the arm is sometimes referred to as a "peripherally inserted central catheter" ("PICC").

In these cases, long-term IV infusion typically requires that the catheter remain in place for many days. In order to secure such a central venous catheter or other catheter types in position at the insertion site of the catheter, the catheter often is provided with an integrated or movable, winged, flexible extension which is sutured to the patient's skin. In other applications, the thin, winged, flexible extension is covered by a more rigid clamp, which provides a friction fit for the catheter/pad combination. The rigid clamp and the flexible pad have lateral, aligned holes in them which allow the combination to be sutured to the patient's skin. Although this technique provides secure installation of the central venous catheter, it obviously is painful and uncomfortable for the patient. This prior retention procedure also is time consuming and inconvenient, poses the risk of needle-stick to the nurse or other medical professional, and risks suture-site infection to the patient.

SUMMARY OF THE INVENTION

A need therefore exists for an anchoring system which quickly and securely attaches a catheter, tube, electrical wire or similar article to the skin of a patient, without suturing.

One aspect of the present invention involves an anchoring system for securing a portion of a medical article to the body of a patient. The anchoring system comprises a base coupled to an adhesive bottom surface. At least two filaments extend from the base. Each filament includes at least one protuberance that is positioned on the filament toward a distal end of the filament. At least two receptacles also are coupled to the base. Each receptacle is arranged so as to cooperate with at least one of the filaments. Each receptacle includes at least one aperture which receives the respective filament distal end and protuberance. The aperture cooperates with the protuberance to inhibit retraction of the filament distal end from the receptacle.

In accordance with another aspect of the present invention, an anchoring system is provided for securing a portion of a medical article to the body of a patient. The anchoring system comprises a base coupled to an adhesive bottom surface. An elongated thread extends from the base. A corresponding receptacle is also connected to the base at a position spaced from the thread. The receptacle is configured to receive at least a distal end of the thread with structure on the thread and receptacle interengaging. This interengaging structure of the thread and receptacle permits insertion of the thread's distal end into the receptacle but inhibits retraction of thread's distal end from the receptacle.

BRIEF DESCRIPTION OF THE DRAWINGS

These and other features of the invention will now be described with reference to the drawings of a preferred embodiment which is intended to illustrate and not to limit the invention, and in which.

DETAILED DESCRIPTION OF A PREFERRED EMBODIMENT

Figure 1:
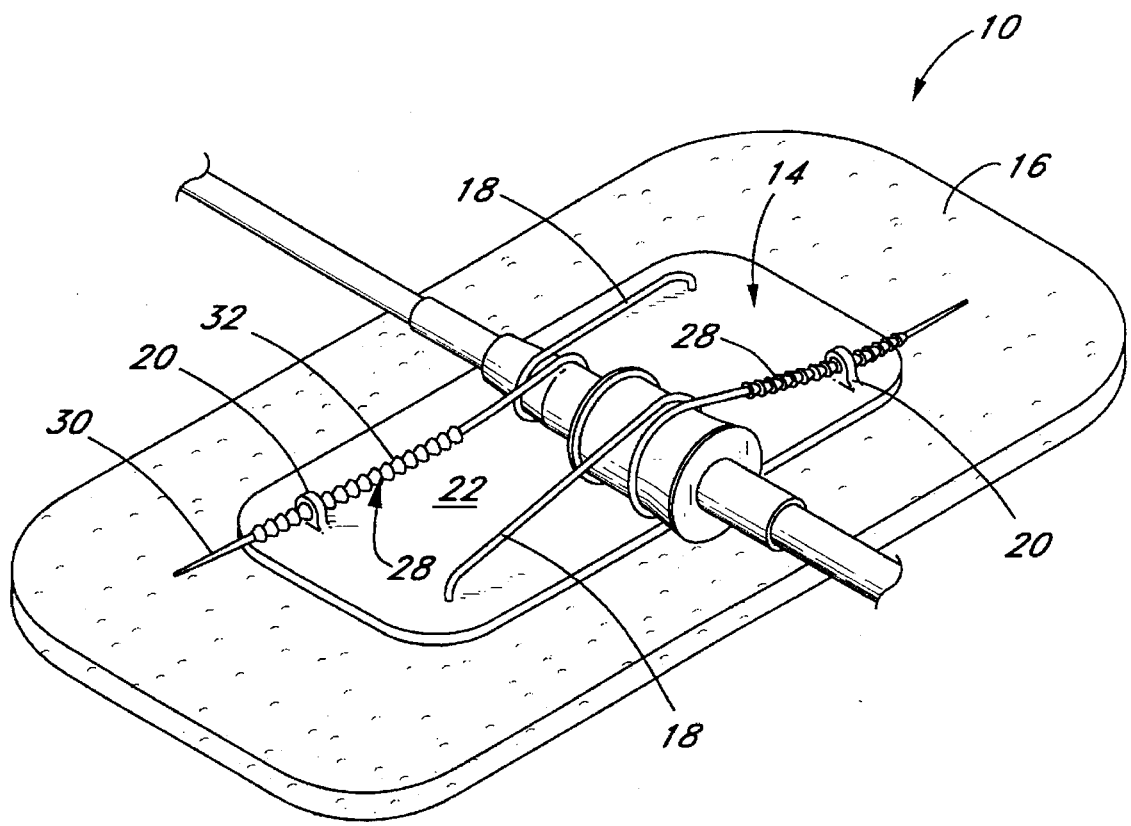
FIG. 1 is a perspective view of an anchoring system in accordance with a preferred embodiment of the present invention, together with an exemplary catheter and fluid tube coupling.

FIG. 1 illustrates an anchoring system 10 which is configured in accordance with a preferred embodiment of the present invention and is used in connection with a catheter-fluid line connector 12 (e.g., a lure-lock connector). It is understood, however, that the present anchoring system 10 also can be successfully utilized in connection with other types of medical articles, such as for example, but without limitation, CVCs, PICCs, and hemodialyses catheters, as well as with electrical wires or cables connected to external or implanted electronic devices or sensors. Thus, as used herein, the term "medical article" is meant generically to include catheters, fluid supply and drainage lines, connectors, adaptors, electrical wires and cables, and the like, all of which may be retained by the present anchoring system 10. It therefore should be understood that the principles of the present invention are not limited to PICCs or central line catheters.

Figure 2:
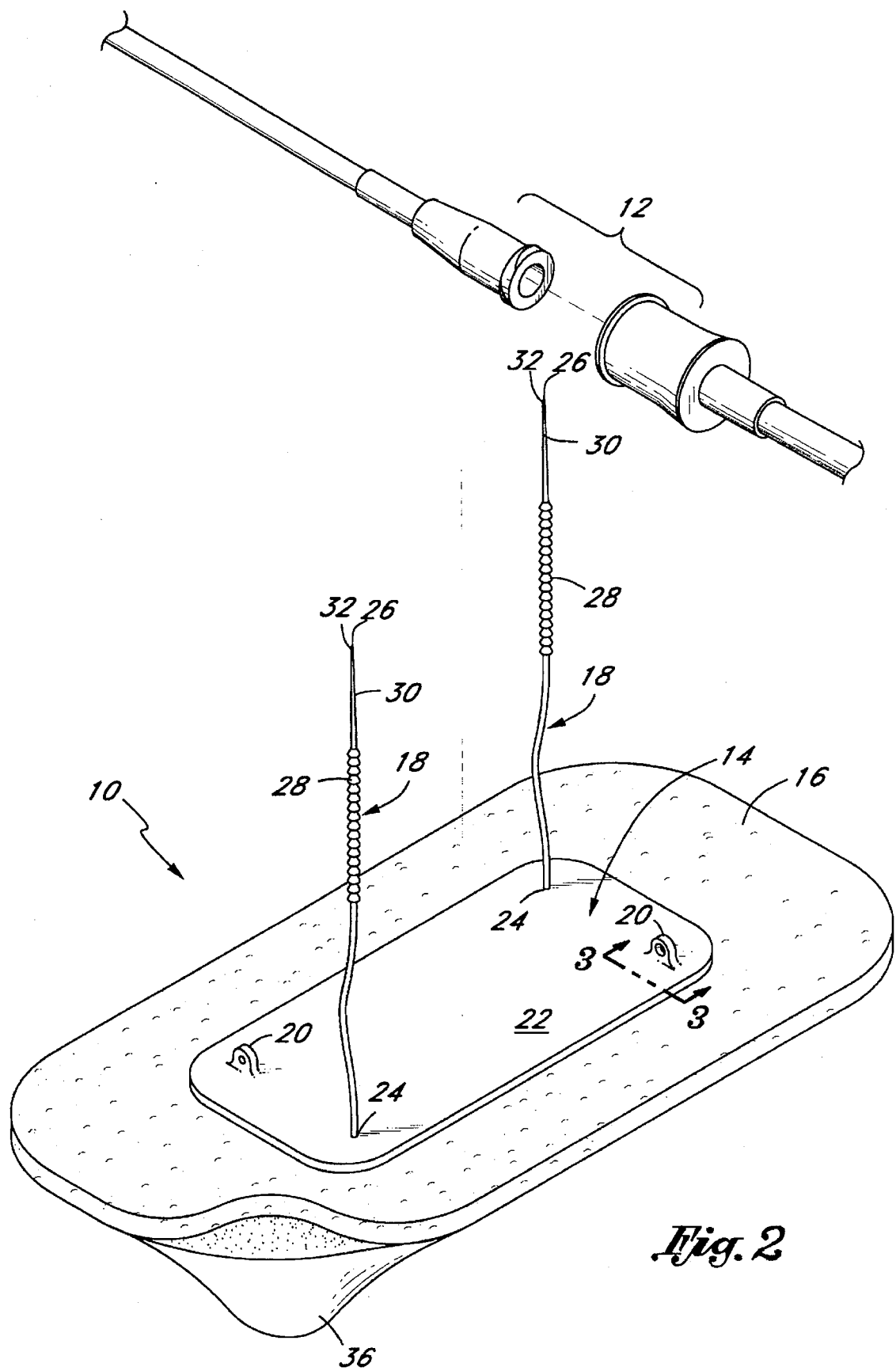
FIG. 2 is an exploded perspective view of the anchoring system and the catheter and fluid tube coupling of FIG. 1.

With reference to FIG. 2, the anchoring system 10 includes a retention mechanism 14 mounted on top of an anchor pad 16. The anchor pad 16 includes a self-adhesive backing (not shown) to secure the retention mechanism 14 to the patient's skin. The retention mechanism 14 includes at least one filament or thread 18 which cooperates with a corresponding receptacle 20. By means of cooperation between the filament 18 and the receptacle 20, as described below in more detail, the connector 12 can be conveniently and painlessly anchored to and released from the patient's skin.

In the illustrated embodiment, the retention mechanism 14 includes a base 22 and a pair of filaments 18 that extend from the base 22. The retention mechanism 14 of course can include other numbers of filaments 18 in order to suit a specific application. Each filament 18 includes a fixed proximal end 24, a free distal end 26 and at least one protuberance (generally indicated by reference numeral 28) positioned therebetween. In the illustrated embodiment, each filament 18 includes a plurality of protuberances 28 arranged in series between the distal end 26 and the proximal end 24 of the filament 18.

As seen in FIG. 2, the protuberances 28 generally have identical barb-like shapes. In the illustrated embodiment, each protuberance 28 of the filament 18 has a generally conical shape with a maximum diameter at a proximal end of the protuberance 28. Although not illustrated, the protuberances 28 can take a variety of other shapes, such as for example, hollow conical shapes, arrow shapes, or transverse rib-like shapes. The proximal end of each protuberance 28, however, desirably has a diameter which is larger than the diameter of the filament 18. As such, in the illustrated embodiment, the proximal end of each protuberance 28 forms a flat surface that lies generally transverse to a longitudinal axis of the corresponding filament 18. The proximal end surface of some or all of the protuberances alternatively can slop or project toward the distal end of the filament 18.

The filament 18 desirably includes a needle-like shaped distal portion 30 with a generally pointed, but blunt end 32 portion positioned at the distal end of the filament 18. The distal portion 30 smoothly tapers with increasing diameter from the end 32 toward the distal-most protuberance 28. The diameter of the distal portion 30 at a point adjacent the distal-most protuberance 28 desirably equals the diameter of the filament 18 proximal to the protuberances 28.

The retention mechanism 14 also includes at least one and preferably a plurality of receptacles 20 positioned on the base 22. Each receptacle 20 is arranged on the base 22 to cooperate with at least one filament 18, as discussed below.

The receptacles 20 receive the distal ends 26 of the filaments 18 in a manner permitting the insertion of the filament 18 into the receptacle 20, but inhibiting the retraction of the filament 18 from the receptacle 20. For this purpose, the corresponding filament 18 and receptacle 20 include interengaging structure that allows the filament 18 distal end to be easily inserted into the receptacle 20 in one direction with a first degree of force but prevents retraction of the filament 18 distal end when a same degree of force is applied to the filament 18 in the opposite direction. A larger degree of force is required to retract the filament 18 distal end from the receptacle 20.

In the illustrated embodiment, the interengaging structure between the corresponding filament 18 and the receptacle 20 comprises the protuberances on the filaments 18 and apertures 34 of the receptacles 20. Again, the interengaging structures of the filament-receptacle pairings are substantially identical, and the following description of one should be understood as applying equally to both, unless specified to the contrary.

Figure 3:
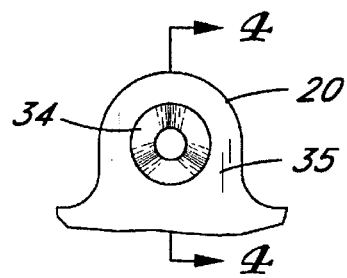
FIG. 3 is a side plane view of a receptacle of the anchoring system of FIG. 2 as viewed in the direction of line 3—3.
Figure 4:
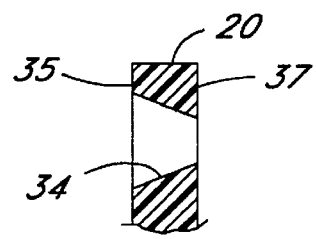
FIG. 4 is a cross-sectional view of the receptacle of FIG. 3 taken along line 4—4.

As best seen in FIGS. 3 and 4, each aperture 34 advantageously has a conical or funnel-like shape to help guide the distal end 32 of the filament distal portion 30 through the aperture 34. The aperture 34 tapers from a large diameter on an inner side 35 of the receptacle to a smaller diameter of the outer side 37 of the receptacle 34. The smaller diameter desirably is larger than the maximum diameter of the filament distal portion 30, but smaller than the maximum diameter of the protuberances 28 on their proximal sides.

The receptacle 20 and/or the protuberances 28 are configured such that the wall on the outer side 37 of the receptacle 20 about the aperture 34 and/or the protuberances 28 deflect to allow the larger diameter protuberances 28 to pass through the smaller diameter aperture 34 on the outer side 37 of the receptacle 20. In the illustrated embodiment, the thin wall about the aperture 34 at its outer side, the thin peripheral thickness of the protuberance 28 at its proximal end, and the elastic nature of the plastic which form these components provides the required deflection necessary for the protuberances 28 to pass through the aperture 34. Once the protuberance 28 passes through the small end of the aperture 34, the protuberance 28 and receptacle 20 spring back to inhibit retraction of the protuberance 28 through the aperture 34.

Figure 5:
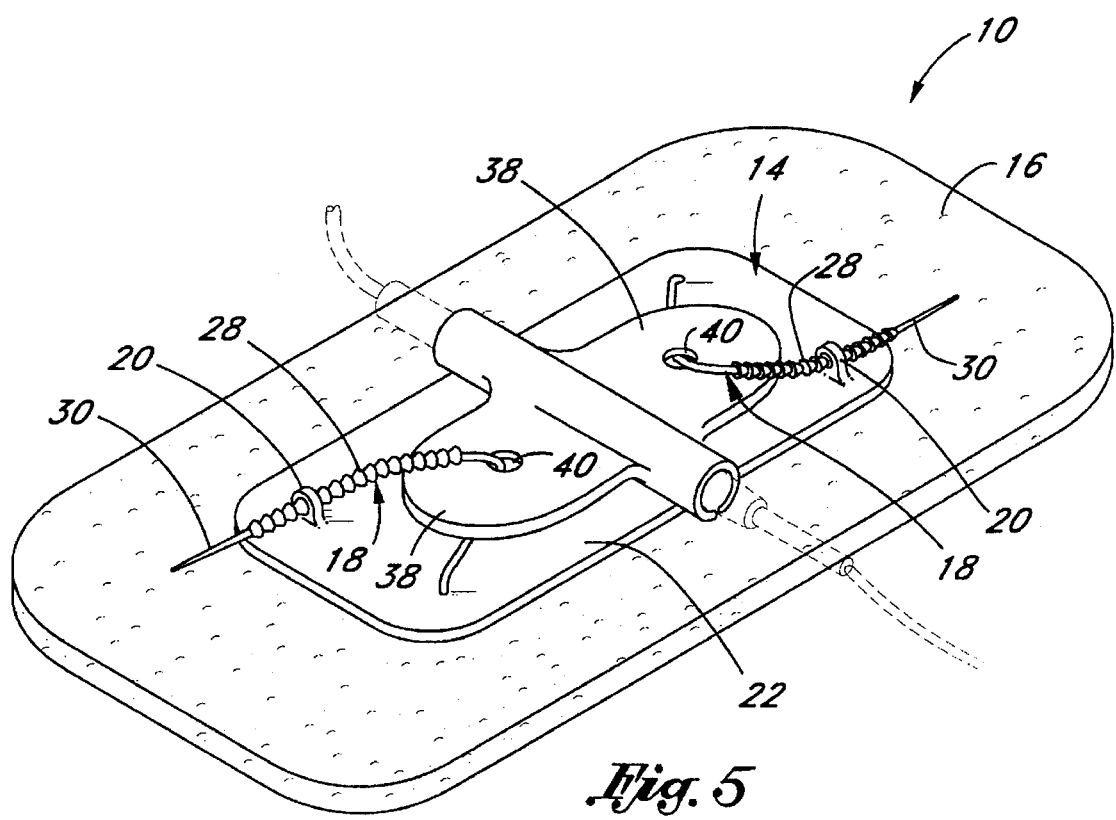
FIG. 5 is a perspective view of the anchoring system of FIG. 1 engaged with a conventional suture wing extension.

With reference to FIG. 1, each filament 18 and corresponding receptacle 20 are positioned on opposite of the base 22. In the illustrated embodiment, the filaments 18 also are positioned on opposite sides of the base 22 from each other, and the receptacles 20 are positioned on opposite sides of the base 22 from each other. The filaments 18 and the receptacles 20 advantageously are placed proximate to the corners of the base 22 with the filaments 18 positioned diagonally across the base 22 from each other and the receptacles 20 positioned diagonally across the base 22 from each other. The filaments 18 and receptacles 20 arranged accordingly define a space in which the catheter/fluid-line connector 12, a suture wing extension (see FIG. 5), or similar medical article can be placed.

The base 22, filaments 18 and receptacles 20 of the retention mechanism 14 desirably are integrally formed together. This can be accomplished in any of a variety of ways which will be well known to one of sill in the art. For instance, the entire retention mechanism 14 can be integrally molded of plastic by injection molding.

With reference to FIGS. 2, the retention mechanism 14 desirably is secured to the anchor pad 16 by means of cyanoacrylate, or other bonding material. The flexible anchor pad 16 comprises a laminate structure formed by an upper paper or other woven or non-woven cloth layer, an inner cellulose foam layer, and a bottom adhesive layer. Alternatively, the flexible anchor pad 16 may comprise an adhesive bottom layer and an upper cellulose foam layer. An upper surface of the foam layer is roughened by corona treating the foam with a low electric charge, as known in the art. The roughened or porous upper surface of the anchor pad 16 improves cyanoacrylate (other types of adhesive or bonding materials) adhesion when attaching the retainer to the anchor pad 16.

A removable paper or plastic backing 36 desirably covers the bottom adhesive surface before use. The backing preferably resists tearing and is divided into a plurality of pieces to ease attachment of the pad 16 to the patient's skin. Desirably, the backing 36 is split along a center line of the flexible anchor pad 16 in order to expose only half of the adhesive bottom surface at one time. Although not illustrated, the backing 36 also advantageously can extend beyond at least one edge of the anchor pad 16 to ease removal of the backing from the adhesive layer.

In operation, the self-adhesive anchor pad 16 is applied to the skin of the patient in the vicinity of the connector 12. The anchor pad 16 should be mounted on the patient so that the filaments 18 and receptacles 20 are positioned on either side of the connector 12 and lies directly under it.

A first filament 18 is wrapped around one side of the connector 12 and is threaded through the opposing receptacle 20. As understood from FIG. 1, the filament 18 has a sufficiently long length to wrap around the connector 12 and easily threaded through the receptacle 20.

The distal end 26 of the filament 18 threads into the receptacle aperture 34 easily. The conical shape of the aperture 34 helps guide the distal portion 30 through the receptacle 20. The conical shape of the protuberances 28 further ease insertion of the filament 18 through the aperture 34, as described above. The flat proximal end of the protuberance 28, however, engages the outer surface 37 of the receptacles 20 and inhibits retraction of the filament 18 from the receptacle 20.

The healthcare provider likewise wraps the second filament 18 around the other side of the fluid line connector 12 and then inserts the distal end 26 into the opposing receptacle 20. The insertion process is accomplished in the manner described above. Excess filament length can be severed or cut distal to the receptacle 20.

The healthcare provider pulls both filaments 18 tight to draw the fluid line connector 12 against the base 22. The taut filaments 18 prevent the fluid line connector 12 from moving transversely away from the base 22 and from sliding either longitudinally or laterally over the base 22. In this manner, the anchoring system 10 assists maintaining the connection between the catheter and fluid line established by the connector 12.

FIG. 3 also illustrates that the present anchoring system 10 can be used to secure to a patient a conventional suture wing extensions 38, such as, for example, that used with a Quinton® Hemodialysis catheter or a Cook® PICC, or another type suture seat, such as, for example, that used with the Baxter® Triple Lumen (not illustrated). A healthcare provider places the suture wing extensions 38 on the base 22 between the filaments 18 and receptacles 20. One of the filaments 18 is threaded through the closest suture hole 40 of the suture wing and threaded through the adjacent receptacle 20. Likewise, the healthcare provider inserts the second filament 18 through the corresponding suture hole 40 and receptacle 20. The interengaging structures of the filaments 18 and the corresponding receptacles 20 prevent unintentional disengagement of the filaments 18 from the receptacles 20.

This application of the anchoring system 10 illustrates that each filament 18 can be inserted into either receptacle 20 to permit the anchoring system 10 to be used with more than one type of medical article. When used with the opposing receptacle 20, the filament 18 can be wrapped around a portion of the medical article and threaded through the corresponding receptacle 20. When used with the adjacent receptacle 20, the filament 18 engages the structure on one side of the medical article and then can be threaded through the receptacle 20. Other arrangements of the filaments 18 and receptacles 20 which will be readily apparent to those skilled in the art also are possible in order for the anchoring system 10 to be used with other types of medical articles.

When removal becomes necessary, the healthcare provider snips the filaments 18 at a point between the proximal end 24 of the filament 18 and the corresponding receptacle 20. The medical device then can be lifted from the base 22 and the anchor pad 16 can be peeled from the patient's skin.

Thus, no painful or time-consuming sutures or other extensive procedures involving medial sharps (e.g., suture needles) are necessary to anchor a medical article to a patient's skin. In addition, the anchor pad 16 absorbs any forces which are incurred in the installation or removal of the anchoring system 10 and the medical device, thereby providing greater comfort for the patient.

Although this invention has been described in terms of a certain preferred embodiment, other embodiments apparent to those of ordinary skill in the art are also within the scope of this invention. Accordingly, the scope of the invention is intended to be defined only by the claims which follow.

What is claimed is:

1. An anchoring system for securing a portion of a medical article to a body of a patient, said anchoring system comprising a base coupled to an adhesive layer, at least two filaments extending from said base, said filaments being spaced apart from one another on said base, each filament including a proximal end affixed to the base, a distal end and a plurality of protuberances positioned between the proximal and distal ends of the filament, and at least two receptacles coupled to said base, each receptacle arranged on the base so as to cooperate with at least one of the filaments, each receptacle including at least one aperture which receives the respective filament distal end and at least one of the protuberances, the aperture cooperating with the protuberance to inhibit retraction of the filament digtal end from the receptacle, the filaments, receptacles and base being unitary.

2. An anchoring system as in claim 1, wherein each of said protuberances has a generally conical, barb-like shape.

3. An anchoring system as in claim 1, wherein on each filament a distal-most protuberance of said plurality of protuberances is spaced from said distal end of said filament.

4. An anchoring system as in claim 3, wherein each filament includes a distal portion having a needle-like shape which increases in diameter from the distal end of the filament, which has a generally pointed shape, in a direction toward said protuberances.

5. An anchoring system as in claim 4, wherein each aperture has a generally conical shape that tapers from a large diameter to a small diameter, said small diameter being larger than the diameter of said distal portion of said filament.

6. An anchoring system as in claim 1, wherein said protuberances of each filament are arranged in series along a portion of said filament.

7. An anchoring system as in claim 1, wherein said protuberances decrease in size toward said distal end of the filament.

8. An anchoring system as in claim 1, wherein at least one of said protuberances is configured to be drawn through the aperture of the corresponding receptacle in one direction with a first degree of force and retracted through the aperture in an opposite direction with a second degree of force, said second degree of force being larger than said first degree of force.

9. An anchoring system as in claim 1, wherein each filament is arranged on said base so as to cooperate with at least two receptacles.

10. An anchoring system as in claim 1, wherein said filaments and said receptacles are spaced apart from each other on said base and are adapted to permit the portion of the medical article to lie on said base between the corresponding filament and receptacle pairings.

11. An anchoring system as in claim 1, wherein each filament is positioned on one side of said base with one receptacle positioned next to said filament and another receptacle positioned directly opposite said filament.

12. An anchoring system as in claim 1 additionally comprising a flexible anchor pad supporting the base, said adhesive layer extending over at least a portion of one side of said anchor pad with the base being positioned on an opposite side of said anchor pad.

13. The anchoring system as in claim 12, wherein said anchor pad has a laminate structure formed by a cellulose foam layer interposed between said adhesive layer and a layer of woven fibers.

14. An anchoring system as in claim 1, wherein said protuberances all have similar shapes.

15. An anchoring system for securing a portion of a medical article to a body of a patient, said anchoring system comprising a base coupled to an adhesive layer, an elongated filament extending from said base and a corresponding receptacle connected to said base at a position spaced from said filament, said receptacle configured to receive a distal end of said filament, said filament including a plurality of protuberances positioned between a proximal end fixed to the base and a free distal end, and said receptacle including a conical shaped receptor which cooperates with the protuberances to permit insertion of the filament distal end into said receptacle but inhibit retraction of filament distal end from said receptacle.

16. An anchoring system as in claim 15, wherein said protuberance generally has a barb-like shape.

17. An anchoring system as in claim 15, wherein said plurality of protuberances are similarly shaped.

18. An anchoring system as in claim 17, wherein said protuberances are arranged in series along a portion of said filament.

19. An anchoring system as in claim 15 additionally comprising a flexible anchor pad supporting the base, said adhesive layer extending over at least a portion of one side of said anchor pad with the base being positioned on an opposite side of said anchor pad.

20. The anchoring system as in claim 19, wherein said anchor pad has a laminate structure formed by a cellulose foam layer interposed between said adhesive layer and a layer of woven fibers.

21. The anchoring system as in claim 15, wherein said base, thread and receptacle are integrally formed together.

22. An anchoring system as in claim 15, wherein said protuberance is spaced from said distal end of said filament.

23. An anchoring system as in claim 22, wherein said filament includes a distal portion having a needle-like shape which increases in diameter from the distal end of the filament, which has a generally pointed shape, in a direction toward said protuberances.

24. An anchoring system as in claim 15, wherein at least one of said protuberances is configured to be drawn through the receptor of the corresponding receptacle in one direction with a first degree of force and through the receptor in an opposite direction with a second degree of force, and the second degree of force is larger than the first degree of force.

* * * * *

UNITED STATES PATENT AND TRADEMARK OFFICE
CERTIFICATE OF CORRECTION

PATENT NO. : 5,637,098
DATED : June 10, 1997
INVENTOR(S) : Steven F. Bierman, M.D.

It is certified that error appears in the above-identified patent and that said Letters Patent is hereby corrected as shown below:

In Claim 1, column 6, line 9, "digtal end" should be --distal end--.
In Claim 15, column 7, line 6, "of filament" should be --of the filament--.

Signed and Sealed this

Twenty-sixth Day of May, 1998

*Attest:*

BRUCE LEHMAN

*Attesting Officer*  *Commissioner of Patents and Trademarks*